United States Patent
Rodriguez et al.

(10) Patent No.: US 8,935,140 B2
(45) Date of Patent: *Jan. 13, 2015

(54) GENERATING INVISCID AND VISCOUS FLUID-FLOW SIMULATIONS OVER A SURFACE USING A FLUID-FLOW MESH

(71) Applicant: Aerion Corporation, Reno, NV (US)

(72) Inventors: David L. Rodriguez, Palo Alto, CA (US); Peter Sturdza, Redwood City, CA (US)

(73) Assignee: Aerion Corporation, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,189

(22) Filed: May 3, 2013

(65) Prior Publication Data

US 2013/0246027 A1 Sep. 19, 2013

Related U.S. Application Data

(63) Continuation of application No. 12/982,744, filed on Dec. 30, 2010, now Pat. No. 8,457,939.

(51) Int. Cl.

| G06F 7/60 | (2006.01) |
| G06F 17/10 | (2006.01) |
| G06G 7/48 | (2006.01) |
| G06G 7/56 | (2006.01) |
| G06G 7/50 | (2006.01) |
| G06F 17/50 | (2006.01) |
| G06F 17/18 | (2006.01) |
| G06F 19/00 | (2011.01) |

(52) U.S. Cl.
CPC ........ G06F 17/5009 (2013.01); G06F 17/5018 (2013.01); G06F 17/5095 (2013.01); *G06F 17/18* (2013.01); *G06F 19/704* (2013.01); *G06F 2217/16* (2013.01); *G06F 2217/46* (2013.01)
USPC .................. 703/9; 703/2; 703/5; 703/6

(58) Field of Classification Search
CPC . G06F 17/5009; G06F 17/5018; G06F 17/18; G06F 19/704
USPC .................................. 703/2, 5, 6, 9
See application file for complete search history.

(56) References Cited

U.S. PATENT DOCUMENTS

| 5,544,524 A | 8/1996 | Huyer et al. |
| 5,901,928 A | 5/1999 | Raskob, Jr. |

(Continued)

OTHER PUBLICATIONS

Aftosmis et al. "Applications of a Cartesian Mesh Boundary-Layer Approach for Complex Configurations", 44th AIAA Aerospace Sciences Meeting, Reno NV, Jan. 9-12, 2006.*

(Continued)

*Primary Examiner* — Omar Fernandez Rivas
*Assistant Examiner* — Angel Calle
(74) *Attorney, Agent, or Firm* — Morrison & Foerster LLP

(57) ABSTRACT

Fluid-flow simulation over a computer-generated surface is generated using inviscid and viscous simulations. A fluid-flow mesh of fluid cells is obtained. At least one inviscid fluid property for the fluid cells is determined using an inviscid fluid simulation that does not simulate fluid viscous effects. A set of intersecting fluid cells that intersects the surface are identified. A surface mesh polygon of the surface mesh is identified for each intersecting fluid cell. At least one boundary-layer fluid property for each identified surface mesh polygon is determined using the at least one inviscid fluid property of the corresponding intersecting fluid cell and a boundary-layer simulation that simulates fluid viscous effects.

20 Claims, 12 Drawing Sheets

(56) References Cited

U.S. PATENT DOCUMENTS

| | | | |
|---|---|---|---|
| 5,926,399 A * | 7/1999 | Berkooz et al. | 703/7 |
| 6,445,390 B1 * | 9/2002 | Aftosmis et al. | 345/421 |
| 6,516,652 B1 | 2/2003 | May et al. | |
| 7,054,768 B2 | 5/2006 | Anderson | |
| 7,243,057 B2 * | 7/2007 | Houston et al. | 703/9 |
| 7,251,592 B1 | 7/2007 | Praisner et al. | |
| 7,430,500 B2 * | 9/2008 | Lei et al. | 703/9 |
| 7,565,276 B2 * | 7/2009 | Song et al. | 703/2 |
| 7,813,907 B2 * | 10/2010 | Zhang et al. | 703/9 |
| 7,880,883 B2 * | 2/2011 | Okcay et al. | 356/432 |
| 7,912,681 B2 * | 3/2011 | Narramore et al. | 703/1 |
| 7,921,002 B2 * | 4/2011 | Kamatsuchi | 703/9 |
| 8,115,766 B2 * | 2/2012 | Svakhine et al. | 345/426 |
| 8,259,104 B2 * | 9/2012 | Pirzadeh et al. | 345/419 |
| 2004/0138853 A1 * | 7/2004 | Tanahashi et al. | 702/179 |
| 2004/0167757 A1 * | 8/2004 | Struijs | 703/2 |
| 2005/0098685 A1 | 5/2005 | Segota et al. | |
| 2005/0246110 A1 * | 11/2005 | van Dam et al. | 702/45 |
| 2006/0025973 A1 | 2/2006 | Kim | |
| 2007/0034746 A1 | 2/2007 | Shmilovich et al. | |
| 2008/0061192 A1 | 3/2008 | Sullivan | |
| 2008/0163949 A1 | 7/2008 | Duggleby et al. | |
| 2008/0177511 A1 | 7/2008 | Kamatsuchi | |
| 2008/0300835 A1 | 12/2008 | Hixon | |
| 2009/0065631 A1 | 3/2009 | Zha | |
| 2009/0142234 A1 * | 6/2009 | Tatarchuk et al. | 422/122 |
| 2009/0171596 A1 | 7/2009 | Houston | |
| 2009/0171633 A1 | 7/2009 | Aparicio Duran et al. | |
| 2009/0234595 A1 | 9/2009 | Okcay et al. | |
| 2009/0312990 A1 | 12/2009 | Fouce et al. | |
| 2010/0036648 A1 | 2/2010 | Mangalam et al. | |
| 2010/0250205 A1 | 9/2010 | Velazquez Lopez et al. | |
| 2010/0268517 A1 | 10/2010 | Calmels | |
| 2010/0276940 A1 | 11/2010 | Khavari et al. | |
| 2010/0280802 A1 | 11/2010 | Calmels | |
| 2010/0305925 A1 | 12/2010 | Sendhoff et al. | |
| 2011/0288834 A1 * | 11/2011 | Yamazaki et al. | 703/2 |
| 2012/0065950 A1 * | 3/2012 | Lu | 703/2 |
| 2012/0173219 A1 * | 7/2012 | Rodriguez et al. | 703/9 |
| 2012/0245903 A1 * | 9/2012 | Sturdza et al. | 703/2 |

OTHER PUBLICATIONS

Kravtsova et al. "An effective numerical method for solving viscous_inviscid interaction problems", Phil. Trans. R. Soc. A 2005 363, 1157-1167.*

Veldmann et al. "Interaction Laws in Viscous-Inviscid Coupling", 2004.*

May et al. "Unstructured Algorithms for Inviscid and Viscous Flows Embedded in a Unified Solver Architecture: Flo3xx", 43rd Aerospace Sciences Meeting and Exhibit, Jan 10-13, 2005, Reno, NV.*

Neel, Reece. "Advances in Computational Fluid Dynamics: Turbulent Separated Flows and Transonic Potential Flows", 1997.*

Lagree, P. "Interactive Boundary Layer [IBL] or Inviscid-Viscous Interactions [IVI or VII]", Dec. 2009.*

"Numerical Simulation of Flows past Bluff Bodies", 2001.*

Arthur E.P. Veldman, NPL, "Quasi-Simultaneous Viscous-Inviscid Interaction for Transonic Airfoil Flow", 2005.*

Notice of Allowance received for U.S. Appl. No. 13/069,374, mailed on May 15, 2013, 23 pages.

Davis et al., "Control of Aerodynamic Flow", AFRL-VA-WP-TR-2005-3130, Delivery Order 0051: Transition Prediction Method Review Summary for the Rapid Assessment Tool for Transition Prediction (RATTraP), Jun. 2005, 95 pages.

Herbert, Thorwald, "Parabolized Stability Equations", Annual Review of Fluid Mechanics, vol. 29, 1997, pp. 245-283.

Jones et al., "Direct Numerical Simulations of Forced and Unforced Separation Bubbles on an Airfoil at Incidence", Journal of Fluid Mechanics, vol. 602, 2008, pp. 175-207.

Khorrami et al., "Linear and Nonlinear Evolution of Disturbances in Supersonic Streamwise Vortices", High Technology Corporation, 1997, 87 pages.

Matsumura, Shin, "Streamwise Vortex Instability and Hypersonic Boundary Layer Transition on the Hyper 2000", Purdue University, Aug. 2003, 173 pages.

Tsao et al., "Application of Triple Deck Theory to the Prediction of Glaze Ice Roughness Formation on an Airfoil Leading Edge", Computers & Fluids, vol. 31, 2002, pp. 977-1014.

"Chapter 3: Numerical Simulation of Flows past Bluff Bodies", 2001, pp. 6-19.

International Search Report and Written Opinion received for PCT Patent Application No. PCT/US2011/067917, mailed on May 1, 2012, 10 pages.

International Search Report and Written Opinion received for PCT Patent Application No. PCT/US2012/030189, mailed on Jun. 20, 2012, 7 pages.

International Search Report and Written Opinion received for PCT Patent Application No. PCT/US2012/030427, mailed on Jun. 20, 2012, 9 pages.

International Search Report and Written Opinion received for PCT Patent Application No. PCT/US2012/028606, mailed on Jun. 1, 2012, 11 pages.

Non Final Office Action received for U.S. Appl. No. 12/982,744, mailed on Oct. 2, 2012, 9 pages.

Notice of Allowance received for U.S. Appl. No. 12/982,744, mailed on Feb. 5, 2013, 8 pages.

Aftosmis et al., "Applications of a Cartesian Mesh Boundary-Layer Approach for Complex Configurations", 44th AIAA Aerospace Sciences Meeting, Reno NV, Jan. 9-12, 2006, pp. 1-19.

Balay et al., "PETSc Users Manual", ANL-95/11, Revision 3.1, Mar. 2010, pp. 1-189.

Bartels et al., "CFL3D Version 6.4—General Usage and Aeroelastic Analysis", NASA/TM-2006-214301, Apr. 2006, 269 pages.

Carter, James E., "A New Boundary-Layer Inviscid Iteration Technique for Separated Flow", AIAA 79-1450, 1979, pp. 45-55.

Cebeci et al., "VISCID/INVISCID Separated Flows", AFWAL-TR-86-3048, Jul. 1986, 95 pages.

Coenen et al., "Quasi-Simultaneous Viscous-Inviscid Interaction for Three-Dimensional Turbulent Wing Flow", ICAS 2000 Congress, 2000, pp. 731.1-731.10.

Crouch et al., "Transition Prediction for Three-Dimensional Boundary Layers in Computational Fluid Dynamics Applications", AIAA Journal, vol. 40, No. 8, Aug. 2002, pp. 1536-1541.

Dagenhart, J. Ray, "Amplified Crossflow Disturbances in the Laminar Boundary Layer on Swept Wings with Suction", NASA Technical Paper 1902, Nov. 1981, 91 pages.

Drela, Mark, "Two-Dimensional Transonic Aerodynamic Design and Analysis Using the Euler Equations", Ph.D. thesis, Massachusetts Institute of Technology, Dec. 1985, pp. 1-159.

Drela et al., "Viscous-Inviscid Analysis of Transonic and Low Reynolds Number Airfoils", AIAA Journal, vol. 25, No. 10, Oct. 1987, pp. 1347-1355.

Drela, Mark, "XFOIL: An Analysis and Design System for Low Reynolds Number Airfoils", Proceedings of the Conference on Low Reynolds Number Aerodynamics, 1989, pp. 1-12.

Drela, Mark, "Implicit Implementation of the Full en Transition Criterion", 21st Applied Aerodynamics Conference, AIAA Paper 2003-4066, Jun. 23-26, 2003, pp. 1-8.

Eymard et al., "Discretization Schemes for Heterogeneous and Anisotropic Diffusion Problems on General Nonconforming Meshes", Available online as HAL report 00203269, Jan. 22, 2008, pp. 1-28.

Fuller et al., "Neural Network Estimation of Disturbance Growth Using a Linear Stability Numerical Model", American Institute of Aeronautics and Astronautics, Inc., Jan. 6-9, 1997, pp. 1-9.

Gaster, M., "Rapid Estimation of N-Factors for Transition Prediction", 13th Australasian Fluid Mechanics Conference, Dec. 13-18, 1998, pp. 841-844.

Gleyzes et al., "A Calculation Method of Leading-Edge Separation Bubbles", Chapter 8, Numerical and Physical Aspects of Aerodynamic Flows II, 1984, pp. 173-192.

Hess et al., "Calculation of Potential Flow About Arbitrary Bodies", Progress in Aerospace Sciences, 1967, pp. 1-138.

Jespersen et al., "Recent Enhancements to OVERFLOW", AIAA 97-0644, 1997, pp. 1-17.

(56) References Cited

OTHER PUBLICATIONS

Kravtsova et al., "An Effective Numerical Method for Solving Viscous—Inviscid Interaction Problems", Philosophical Transactions of the Royal Society A, vol. 363, May 15, 2005, pp. 1157-1167.

Krumbein, Andreas, "Automatic Transition Prediction and Application to Three-Dimensional Wing Configurations", Journal of Aircraft, vol. 44, No. 1, Jan.-Feb. 2007, pp. 119-133.

Lagree, P. Y., "Interactive Boundary Layer [IBL] or Inviscid-Viscous Interactions [IVI or VII]", Dec. 14, 2009, pp. 1-29.

Langlois et al., "Automated Method for Transition Prediction on Wings in Transonic Flows", Journal of Aircraft, vol. 39, No. 3, May-Jun. 2002, pp. 460-468.

Lewis, R. I., "Vortex Element Methods for Fluid Dynamic Analysis of Engineering Systems", Cambridge University Press, 2005, 12 pages.

Lock et al., "Viscous-Inviscid Interactions in External Aerodynamics", Progress in Aerospace Sciences, vol. 24, 1987, pp. 51-171.

May et al., "Unstructured Algorithms for Inviscid and Viscous Flows Embedded in a Unified Solver Architecture: Flo3xx", 43rd Aerospace Sciences Meeting and Exhibit, American Institute of Aeronautics and Astronautics Paper 2005-0318, Jan. 10-13, 2005, pp. 1-15.

Neel, Reece E., "Advances in Computational Fluid Dynamics: Turbulent Separated Flows and Transonic Potential Flows", Aug. 1997, 272 pages.

Perraud et al., "Automatic Transition Predictions Using Simplified Methods", AIAA Journal, vol. 47, No. 11, Nov. 2009, pp. 2676-2684.

Potsdam, Mark A., "An Unstructured Mesh Euler and Interactive Boundary Layer Method for Complex Configurations", AIAA-94-1844, 12th Applied Aerodynamics Conference, Jun. 20-23, 1994, pp. 1-8.

Rasmussen et al., "Gaussian Processes for Machine Learning", MIT Press, 2006, 266 pages.

Spreiter et al., "Thin Airfoil Theory Based on Approximate Solution of the Transonic Flow Equation", Report 1359—National Advisory Committee for Aeronautics, 1957, pp. 509-545.

Stock et al., "A Simplified en Method for Transition Prediction in Two-Dimensional, Incompressible Boundary Layers", Journal of Flight Sciences and Space Research, Vol. 13, 1989, pp. 16-30.

Sturdza, Peter, "An Aerodynamic Design Method for Supersonic Natural Laminar Flow Aircraft", Stanford University, Dec. 2003, 198 pages.

Veldman, A. E. P., "New, Quasi-Simultaneous Method to Calculate Interacting Boundary Layers", AIAA Journal, vol. 19, No. 1, Jan. 1981, pp. 79-85.

Veldman et al., "The Inclusion of Streamline Curvature in a Quasi-Simultaneous Viscous-Inviscid Interaction Method for Transonic Airfoil Flow", Department of Mathematics, University of Groningen, Nov. 10, 1998, pp. 1-18.

Veldman, Arthur E. P., "A Simple Interaction Law for Viscous—Inviscid Interaction", Journal of Engineering Mathematics, vol. 65, Aug. 14, 2009, pp. 367-383.

Veldman, Arthur E. P., "Quasi-Simultaneous Viscous-Inviscid Interaction for Transonic Airfoil Flow", American Institute of Aeronautics and Astronautics Paper 2005-4801, 4th Theoretical Fluid Mechanics Meeting, Jun. 6-9, 2005, pp. 1-13.

Veldman, Arthur E. P., "Strong Viscous-Inviscid Interaction and the Effects of Streamline Curvature", CWI Quarterly, vol. 10, No. 3&4, 1997, pp. 353-359.

Veldmann et al., "Interaction Laws in Viscous-Inviscid Coupling", 2004, pp. 225-232.

Washburn, Anthony, "Drag Reduction Status and Plans—Laminar Flow and AFC", AIAA-Aero Sciences Meeting, Jan. 4-7, 2011, pp. 1-25.

\* cited by examiner

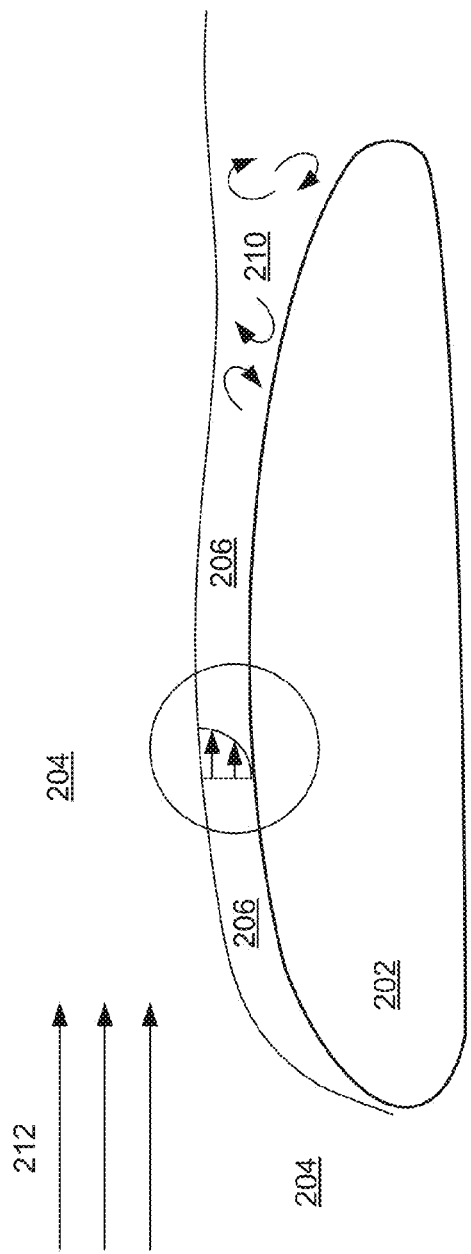
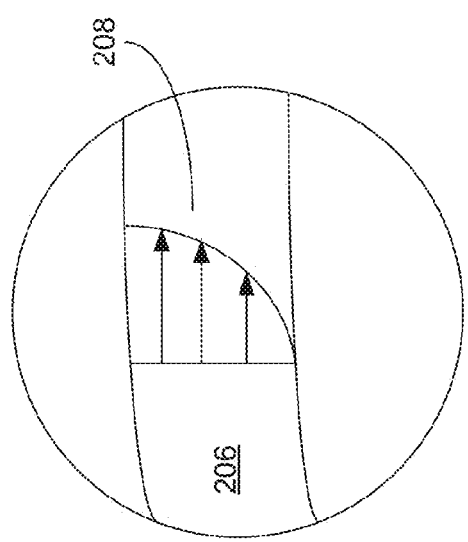

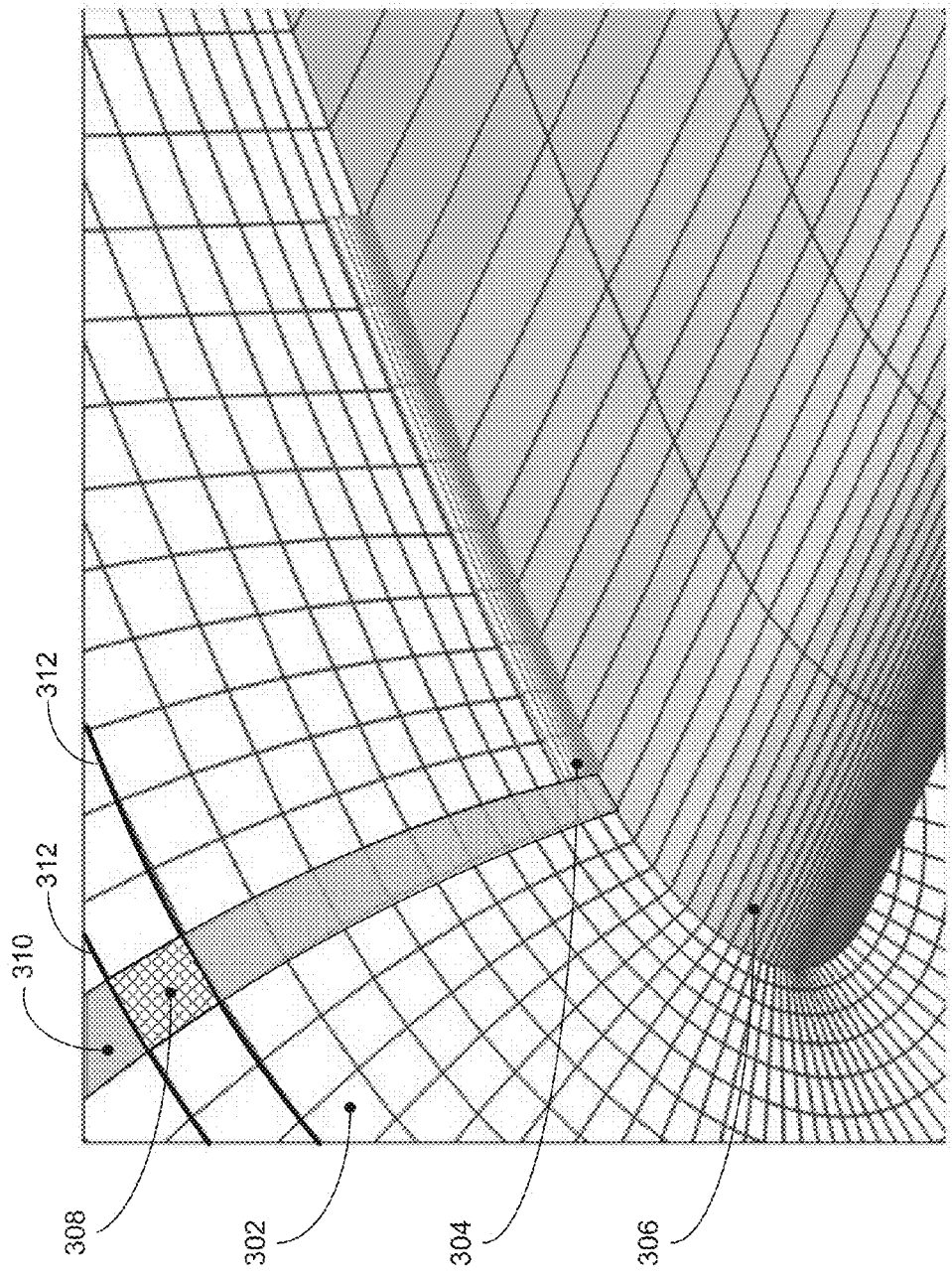

GENERATING INVISCID AND VISCOUS FLUID-FLOW SIMULATIONS OVER A SURFACE USING A FLUID-FLOW MESH

CROSS REFERENCE TO RELATED APPLICATIONS

The present application is a continuation of U.S. application Ser. No. 12/982,744, filed Dec. 30, 2010, which is incorporated herein by reference in its entirety.

BACKGROUND

1. Field

This application relates generally to simulating a fluid flow over an surface and, more specifically, to generating both inviscid and viscous fluid-flow simulations using a fluid-flow mesh.

2. Description of the Related Art

Aerodynamic analysis of an aircraft moving through a fluid typically requires an accurate prediction of the properties of the fluid surrounding the aircraft. Accurate aerodynamic analysis is particularly important when designing aircraft surfaces, such as the surfaces of a wing or control surface. Typically, the outer surface of a portion of the aircraft, such as the surface of a wing, is modeled, either physically or by computer model, so that a simulation of the fluid flow can be performed and properties of the simulated fluid flow can be measured. Fluid-flow properties are used to predict the characteristics of the wing including lift, drag, boundary-layer velocity profiles, and pressure distribution. The flow properties may also be used to map laminar and turbulent flow regions near the surface of the wing and to predict the formation of shock waves in transonic and supersonic flow.

A computer-generated simulation can be performed on a computer-generated aircraft surface to simulate the fluid dynamics of a surrounding fluid. The geometry of the computer-generated aircraft surface is relatively easy to change and allows for optimization through design iteration or analysis of multiple design alternatives. A computer-generated simulation can also be used to study situations that may be difficult to reproduce using a physical model, such as supersonic flight conditions. A computer-generated simulation also allows a designer to measure or predict fluid-flow properties at virtually any point in the model by direct query, without the difficulties associated with physical instrumentation or data acquisition techniques.

In some cases, a computer-generated simulation includes a computational fluid dynamics (CFD) simulation module used to predict the properties of the fluid flow. A CFD simulation module estimates the properties of a simulated fluid flow by applying an algorithm that estimates the interaction between small simulated fluid volumes, also referred to as fluid cells. Because a single CFD simulation module may include millions of individual fluid cells, the complexity of the relationship between fluid cells can have a large effect on the computational efficiency of the simulation. Complex CFD simulation modules can be computationally expensive and require hours or even days to execute using high-performance computer processing hardware.

To reduce the computational burden, in some instances it is desirable to use a CFD simulation module that simplifies the fluid dynamics and produces a fluid simulation that can be solved more rapidly. For example, for fluid flows that are relatively uniform or are located away from an aircraft surface, a simplified simulation that minimizes or ignores fluid properties that have little effect on the overall behavior of the fluid can be used. In this way, processing time is improved without sacrificing accuracy or resolution of the final results.

In other situations, where the fluid flow is not as uniform, it may be necessary to use a CFD simulation module that is more sophisticated and capable of accurately predicting the fluid properties, using more complex fluid dynamics. However, more sophisticated simulation modules are also likely to require more computing resources and therefore require more time to solve.

It may be advantageous to construct a hybrid computer-generated simulation that employs both a simplified CFD simulation module in locations where the fluid flow is relatively uniform, and a more sophisticated CFD simulation module in locations where the fluid dynamics are more complex. By combining different CFD simulation modules, a hybrid computer-generated simulation may increase processing speed while producing accurate results.

Using multiple CFD simulation modules may be difficult, particularly if the CFD simulation modules were not initially designed to work together. The interface between the simulation modules must be constructed so that the resulting computer-generated simulation is both computationally efficient and analytically robust. The techniques described herein solve some of the difficulties in implementing a computer-generated simulation using multiple simulation modules.

SUMMARY

One exemplary embodiment includes a computer-implemented method of generating a fluid-flow simulation over a computer-generated surface, the computer-generated surface comprised of a surface mesh of surface mesh polygons. A fluid-flow mesh is obtained for simulating a fluid flow over the surface, the fluid-flow mesh comprising a plurality of fluid cells. At least one inviscid fluid property for each of the fluid cells is determined using an inviscid fluid simulation that does not simulate fluid viscous effects. A set of intersecting fluid cells, of the plurality of fluid cells, that intersects the surface is identified. A set of surface mesh polygons of the surface mesh are identified. Each surface mesh polygon of the set of surface mesh polygons corresponds to an intersecting fluid cell of the set of intersecting fluid cells. Also, a number of surface mesh polygons of set of surface mesh polygons is fewer than a total number of surface mesh polygons that are intersected by the set of intersecting fluid cells. At least one boundary-layer fluid property for each identified surface mesh polygon is determined using the at least one inviscid fluid property of the corresponding intersecting fluid cell and a boundary-layer simulation that simulates fluid viscous effects.

DESCRIPTION OF THE FIGURES

FIGS. 2a and 2b depict an exemplary fluid flow around a wing surface.

FIG. 3 depicts an exemplary quadrilateral surface mesh and a corresponding structured mesh of the fluid flow.

The figures depict one embodiment of the present invention for purposes of illustration only. One skilled in the art will readily recognize from the following discussion that alternative embodiments of the structures and methods illustrated herein can be employed without departing from the principles of the invention described herein.

DETAILED DESCRIPTION

Figure 1:
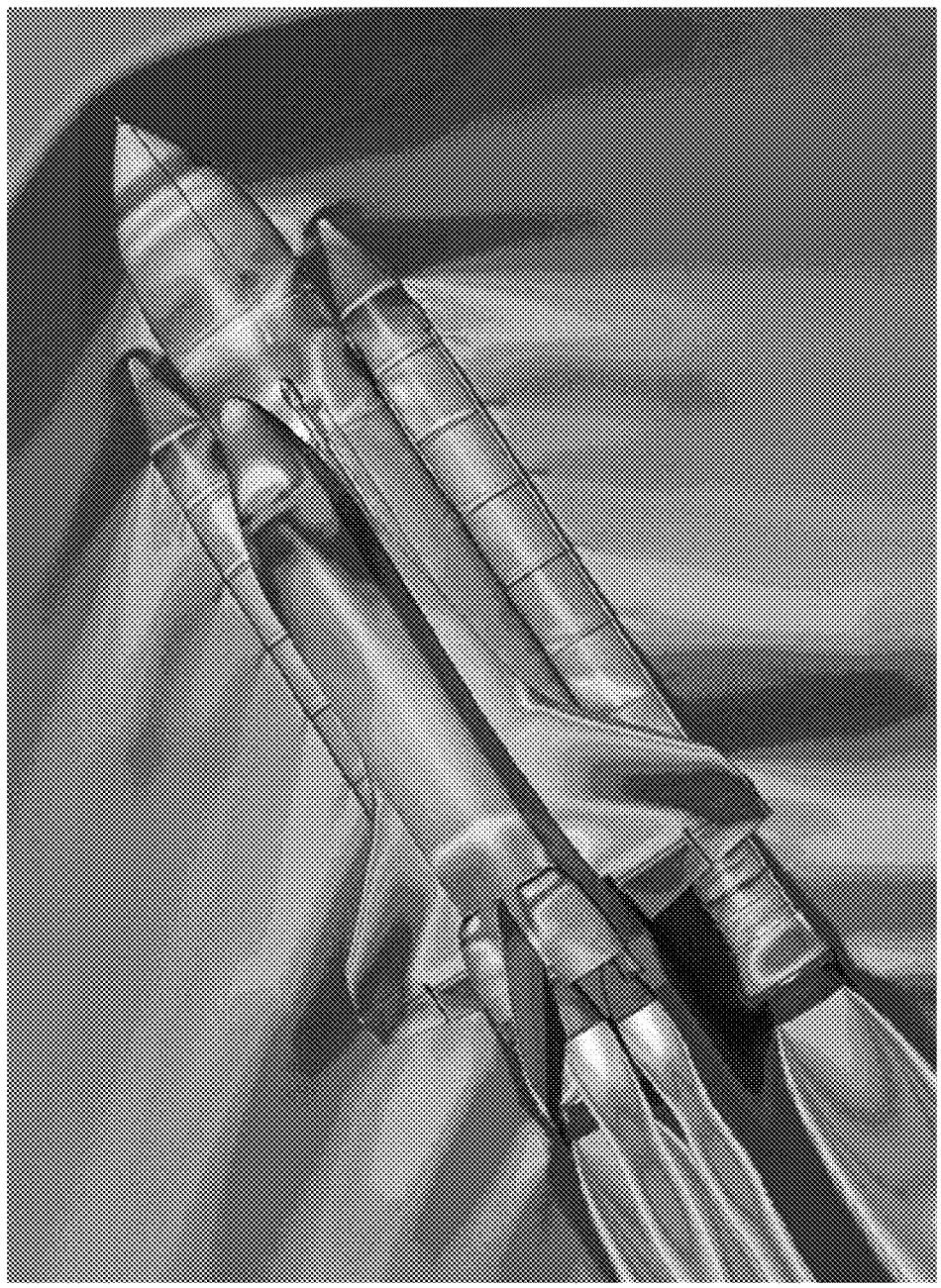
FIG. 1 depicts a computer-generated fluid flow applied to a computer-generated aircraft surface.

As discussed above, a computer-generated simulation can be used to analyze the aerodynamic performance of a proposed aircraft surface, such as a wing or control surface. Using known geometry modeling techniques, a computer-generated aircraft surface that represents the outside surface of the proposed aircraft can be constructed. FIG. 1 depicts an exemplary computer-generated aircraft surface of the Space Shuttle orbiter vehicle, external tank, and twin solid rocket boosters. A CFD fluid simulation module has been applied using the computer-generated aircraft surface of the Space Shuttle orbiter to predict the fluid properties of an exemplary fluid flow.

As shown in FIG. 1, the results of the simulation can be visually represented as shaded regions on the computer-generated aircraft surface of the Space Shuttle. Different shades represent the predicted pressure distribution resulting from the simulated fluid flow. In FIG. 1, transitions between the shaded regions represent locations of predicted pressure change across the surface of the Space Shuttle. Similarly, different pressures in the surrounding fluid flow are represented as differently shaded regions.

In FIG. 1, the simulation of the fluid flow is visualized by depicting the predicted pressure distribution. However, the simulation may be visualized using other fluid properties, including surface velocity, air temperature, air density, and others. Additionally, the simulation may be used to visualize locations of developing shock waves or transitions between laminar and turbulent flow.

The simulation allows the designer or engineer to evaluate the performance of the aircraft geometry for various flow conditions. If necessary, changes can be made to the aircraft geometry to optimize performance or eliminate an unwanted aerodynamic characteristic. Another simulation can be performed using the modified geometry, and the results can be compared. To allow for multiple design iterations, it is advantageous to perform multiple simulations in a short amount of time. However, as described above, there is a tradeoff between speed and accuracy of the simulation depending on the type of CFD simulation module used.

Typically, a computer-generated simulation represents a fluid flow as a three-dimensional fluid-flow mesh of small volumes of fluid called fluid cells. As discussed in more detail below, the shape of the fluid cells can vary depending on the method used to construct the fluid-flow mesh. A CFD simulation module predicts the interactions between the fluid cells in the fluid-flow mesh, using a fundamental algorithm or field equation.

The speed and accuracy of a CFD simulation module depends, in part, on the field equation used to predict the interaction between the flow cells. In some instances, the field equation simplifies the relationship between flow cells by ignoring or minimizing certain dynamic contributions. These field equations are typically less complex, and therefore are more computationally efficient. For instance, a simplified algorithm called the Euler method may be used to simulate a fluid flow when viscous effects can be minimized or ignored. Viscous effects of a fluid can be ignored when, for example, there is not a significant velocity difference between adjacent fluid cells, and therefore shear forces due to internal friction or viscosity are minimal. A CFD simulation module that ignores or minimizes effects of fluid viscosity can also be referred to as an inviscid simulation.

In other instances, a more complex field equation is used to more accurately predict the interaction between the flow cells. For example, a Navier-Stokes method can be used to simulate the pressure and shear forces on the flow cells. Unlike the Euler method mentioned above, the Navier-Stokes method accounts for the effects of viscosity and offers a more accurate simulation of a fluid flow. A simulated fluid flow that accounts for effects due to fluid viscosity can also be referred to as a viscous simulation.

However, the improved accuracy of the Navier-Stokes method comes at the cost of increased computational load, and therefore the Navier-Stokes method is generally slower to compute than an Euler-based algorithm. Thus, selecting the field equation for a CFD module often involves a tradeoff between speed and accuracy. In practice, designers may use faster Euler-based CFD models to evaluate multiple design iterations and then validate the final design iteration with a more accurate Navier-Stokes-based CFD model. However, if the Navier-Stokes CFD simulation reveals a design problem, the entire process must be repeated, wasting valuable time and computing resources.

The techniques described below are computer-generated simulations that use multiple algorithms to achieve acceptable accuracy without requiring the computational burden of a full Navier-Stokes CFD simulation. In many simulations, there is a portion of the flow that can be accurately predicted without taking viscous contributions into account. For example, portions of the fluid flow that are located away from an aircraft surface, such as a wing surface, have a relatively uniform velocity profile. Therefore, an inviscid simulation using, for example, an Euler-based analysis, can be used to accurately predict the behavior of these regions of the fluid flow. In other locations of the fluid flow where there is a less uniform velocity profile, a more complex, viscous simulation can be used.

The techniques described herein provide a method of generating a simulation using more than one field equation to simulate the fluid flow over a computer-generated aircraft surface using a fluid-flow mesh and surface mesh. If the values produced by multiple simulations are not passed between the meshes by using a one-to-one correlation between mesh elements, error and instability may be introduced into the computer model. Many of these errors may be overcome or greatly reduced by establishing a one-to-one correlation between, for example, an inviscid fluid-flow mesh element and surface and surface (or boundary-layer) mesh element. The following technique provides one example of how a one-to-one correlation can be maintained for computer models using a fluid-flow mesh and a surface mesh that do not align.

The following discussion provides an example of a simulated fluid flow over an aircraft surface, such as a wing surface. However, the technique may also be applied to a simulated fluid flow over any type of surface subjected to a fluid flow.

1. Simulating Fluid Flow Over a Wing

FIGS. 2a and 2b depict a two-dimensional representation of a fluid flow over a wing surface 202 classified by two regions: a free stream region 204 and a boundary-layer region 206. As shown in FIGS. 2a and 2b, the boundary-layer region 206 is located near a wing surface 202 and is characterized by a sharply increasing velocity profile 208. Skin friction causes the fluid very close to the wing surface 202 to be essentially zero, with respect to the surface. A sharply increasing velocity profile develops as the velocity increases from a near-zero velocity to the free stream velocity. The sharply increasing velocity profile 208 in the boundary-layer region 206 creates shear forces within the boundary-layer fluid flow. Due to the internal shear forces, viscous properties of the fluid influence the boundary-layer fluid flow. Therefore, a simulation of the flow in the boundary-layer region 206 should account for viscous contributions to the flow dynamics. In some cases, the fluid in boundary-layer region 206 may be characterized as turbulent flow (region 210). Due to fluid voracity, viscous properties of the fluid influence the fluid flow. Thus, a simulation of the turbulent flow should also account for viscous contributions to the flow dynamics. For purposes of this discussion, laminar and turbulent regions are treated as one boundary-layer region and simulated using a single CFD simulation module.

A CFD simulation module that accounts for viscosity may also be called a viscous CFD simulation module or a boundary-layer CFD simulation module. Below, exemplary field equations for a boundary-layer CFD simulation module are provided according to a Drela boundary-layer technique. Drela, M. "XFOIL: An Analysis and Design System for Low Reynolds Number Airfoils," pp. 1-12, Proceedings of the Conference on Low Reynolds Number Aerodynamics (T. J. Mueller ed., Univ. of Notre Dame, Notre Dame, Ind., 1989).

Equation 1, below, represents a boundary-layer integral momentum equation for compressible flow:

$$\frac{d\theta}{dx} + (2 + H - M_e^2)\frac{\theta}{u_e}\frac{du_e}{dx} = \frac{C_f}{2}, \quad \text{Equation 1}$$

where $\theta$ is the momentum thickness, H is the shape factor, $M_e$ is the boundary-layer edge Mach number, $u_e$ is the boundary-layer edge velocity, and $C_f$ is the skin friction coefficient.

Equation 2, below, represents a boundary-layer kinetic energy integral equation:

$$\theta\frac{dH^*}{dx} + (2H^{**} + H^*(1 - H))\frac{\theta}{u_e}\frac{du_e}{dx} = 2C_D - H^*\frac{C_f}{2}. \quad \text{Equation 2}$$

As used in equations 1 and 2, above, shape factors H, H*, and H** are defined as:

$$H = \frac{\delta^*}{\theta} H^* = \frac{\theta^*}{\theta} H^{} = \frac{\delta^{}}{\theta};$$

displacement thickness $\delta^*$ is defined as:

$$\delta^* = \int_0^\infty \left(1 - \frac{\rho u}{\rho_e u_e}\right) dy;$$

momentum thickness $\theta$ is defined as:

$$\theta = \int_o^\infty \left(1 - \frac{u}{u_e}\right)\frac{\rho u}{\rho_e u_e} dy;$$

kinetic energy thickness $\theta^*$ is defined as:

$$\theta^* = \int_o^\infty \left(1 - \left(\frac{u}{u_e}\right)^2\right)\frac{\rho u}{\rho_e u_e} dy;$$

density thickness $\delta^{**}$ is defined as:

$$\delta^{**} = \int_o^\infty \left(1 - \frac{\rho}{\rho_e}\right)\frac{u}{u_e} dy;$$

skin friction coefficient $C_f$ is defined as:

$$C_f = \frac{\tau}{\frac{1}{2}\rho_e u_e^2};$$

and dissipation coefficient $C_D$ is defined as:

$$C_D = \frac{1}{\rho_e u_e^3}\int_o^\infty \tau\frac{\partial u}{\partial y} dy.$$

Solving equations 1 and 2 for local velocity u and density $\rho$, the boundary-layer CFD simulation module can predict the fluid properties for portions of the fluid flow within the boundary-layer region 206. Additionally, characteristics of the boundary layer, including boundary-layer thickness, can also be determined once the fluid properties are known.

The portions of the fluid flow outside of the boundary-layer region 206 may be designated as a free stream region 204. The free stream region 204 is typically located away from the wing surface 202. However, the free stream may be close to the wing surface 202 in areas where the boundary layer is thin or has yet to develop. See, for example, the portion of the fluid flow in FIG. 2a near the leading edge of the wing surface 202. The free stream region 204 is usually characterized as having a relatively uniform velocity profile 212. When there is a uniform velocity profile 212, internal shear forces acting on a fluid may be relatively small, and therefore viscous contributions to the fluid dynamics can be minimized or ignored.

A CFD simulation module that ignores viscous effects may also be called an inviscid CFD simulation module. Equation 3, below, provides an exemplary field equation for an inviscid CFD simulation module. Equation 3, also called the Euler method, represents the conservation of mass, conservation of three components of momentum, and conservation of energy:

$$\frac{\delta m}{\delta t} + \frac{\delta f_x}{\delta x} + \frac{\delta f_y}{\delta y} + \frac{\delta f_z}{\delta z}, \quad \text{Equation 3}$$

-continued where:

$$m = \begin{pmatrix} \rho \\ \rho u \\ \rho v \\ \rho w \\ E \end{pmatrix}; f_x = \begin{pmatrix} \rho u \\ p + \rho u^2 \\ \rho uv \\ \rho uw \\ u(E+p) \end{pmatrix};$$

$$f_y = \begin{pmatrix} \rho v \\ \rho uv \\ p + \rho v^2 \\ \rho vw \\ v(E+p) \end{pmatrix}; f_z = \begin{pmatrix} \rho w \\ \rho uw \\ \rho vw \\ p + \rho w^2 \\ w(E+p) \end{pmatrix};$$

where u, v, and w are components of the velocity vector, p is the pressure, ρ is the density, and E is the total energy per unit volume. Combining Equation 3 with an equation of state (e.g., the ideal gas law), an inviscid CFD simulation module can predict the fluid properties for the free stream fluid region 204.

2. Combining Multiple CFD Simulation Modules

Using the techniques described below, both the boundary-layer and free stream regions can be simulated by combining viscous and inviscid CFD simulation modules. For example, FIG. 3 depicts a fluid flow represented as a structured mesh of inviscid fluid cells 302 and a structured mesh of boundary-layer fluid cells 304. The mesh of inviscid and boundary-layer fluid cells 302 and 304 are depicted in FIG. 3 in a cross-sectional representation (two dimensional). Note, however, that the fluid cells are actually three-dimensional volumes of fluid.

FIG. 3 also depicts a surface mesh 306 of quadrilateral polygons representing the surface of a wing. The surface mesh 306 should approximate the curvilinear shape of the wing surface without creating gaps or breaks between quadrilateral polygons. For relatively simple wing surfaces as shown in FIG. 3, the mesh can be created from multiple wing surface cross-sectional profiles, where each wing profile is approximated by short line segments. The quadrilateral polygons are created by connecting the vertex of each short line segment for adjacent wing profiles.

The structured mesh of inviscid fluid cells 302 shown in FIG. 3 is a mesh of fluid volumes defined using a set of vertices of the surface mesh 306. For a set of four adjacent vertices on the surface mesh 306, a volume 310 is projected from the surface of the wing in a direction as close to a surface normal as possible. The volume is partitioned into fluid cells 308 by defining at least two surfaces 312 that offset a given distance from the surface of the wing. The structured mesh depicted in FIG. 3 does not intersect the surface of the wing represented by the surface mesh 306.

In FIG. 3, the surface mesh 306, the structured mesh of boundary-layer fluid cells 304, and the structured mesh of inviscid fluid cells 302 have been created so that there is a one-to-one correlation to cells at the mesh boundaries. That is, each mesh element that borders another mesh corresponds to exactly one cell of the bordering mesh. Therefore, for a given polygon in the surface mesh, there is one corresponding boundary-layer fluid cell, and for that boundary-layer fluid cell there is one corresponding inviscid fluid cell. This arrangement is advantageous in that it allows data to be passed from one cell to another without having to interpolate or estimate the closest neighboring cells.

The construction of the meshes shown in FIG. 3 typically requires that the surface mesh 306 of the wing be comprised entirely of quadrilateral polygons. The structured mesh of boundary-layer fluid cells 304 and the structured mesh of inviscid fluid cells 302 are then constructed using the vertices of the surface mesh 306 as starting points.

There are, however, drawbacks to using this meshing technique. First, it can be difficult to apply a quadrilateral surface mesh to complex surface geometries. For example, the segmented-line profile technique described above does not work for surfaces without a relatively uniform longitudinal cross section. Also, complex geometries created by intersections between surfaces can be difficult to model using a quadrilateral mesh. For example, a pylori and nacelle hanging off the leading edge of a wing may be difficult to automate and typically requires human interaction or troubleshooting to create a continuous, gap-free surface mesh.

Figure 4:
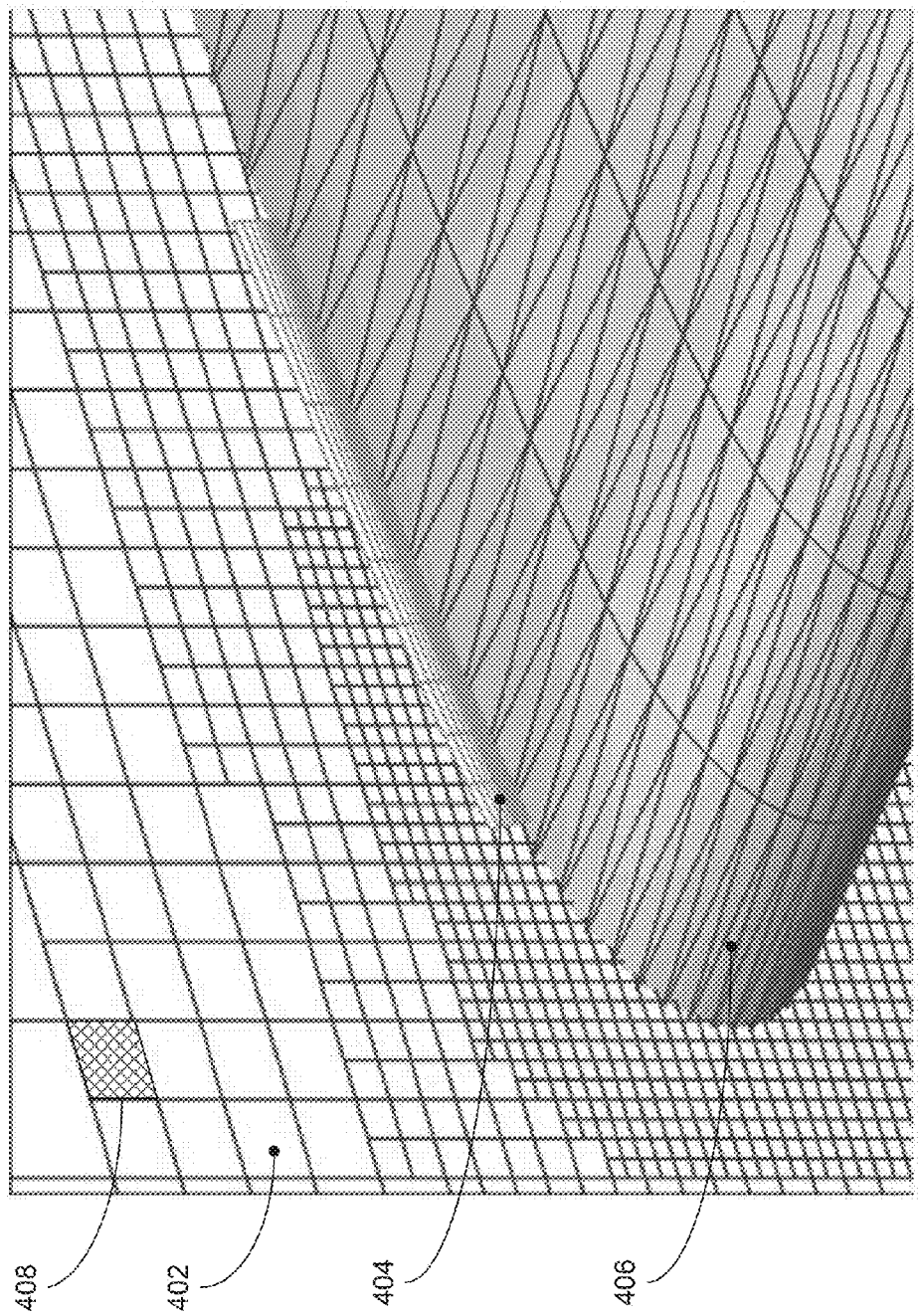
FIG. 4 depicts an exemplary surface mesh and fluid-flow mesh.

FIG. 4 depicts another technique for creating surface and fluid-flow meshes. In FIG. 4, the inviscid portion of the fluid flow is represented by a fluid-flow mesh 402, which is depicted as being a Cartesian mesh. A Cartesian mesh is defined as a mesh of cube or rectangular cuboid fluid cells 408. That is, each fluid cell 408 is bounded by six flat faces where opposite faces are parallel and adjacent faces are orthogonal. In some cases, larger fluid cells are divided into smaller fluid cells by defining additional faces at the midpoint of the existing faces. Thus, the fluid cells in a Cartesian mesh can be different sizes. In the present exemplary embodiment, because the fluid-flow mesh 402 is composed entirely of cube volumes, fluid-flow mesh 402 can be automatically generated minimizing human interaction and troubleshooting. Additionally, cube cells tend to produce less error when using CFD simulation techniques due, in part, to the uniformity of the mesh cells in multiple mesh directions.

FIG. 4 also depicts a surface mesh 406 that is constructed using triangular mesh elements rather than quadrilateral mesh elements. Triangular mesh elements are better suited for representing complex geometries or intersecting surfaces. This technique is also called triangulating the wing surface and can be automated for complex geometries with little or no human intervention.

Compared to the meshing shown in FIG. 3, the meshing technique depicted in FIG. 4 may be easier to create using automated methods and may result in a more consistent, continuous mesh. However, using the meshing technique depicted in FIG. 4, there is no longer a one-to-one correlation between neighboring mesh elements. For example, a given fluid cell in the fluid-flow mesh of boundary-layer fluid cells 404 no longer corresponds to a fluid cell in the fluid-flow mesh 402. A given fluid cell in the fluid-flow mesh of boundary-layer fluid cells 404 also does not correlate to a single surface mesh element on the surface mesh 406 of the wing surface. Additionally, for portions of the fluid-flow mesh 402 near the wing surface, there will be at least some fluid cells that partially intersect one or more of the triangulated surface mesh elements in the surface mesh 406 of the wing surface. Therefore, for any one bordering cell, there are multiple candidate neighboring cells that can be used to exchange data.

Without a one-to-one correlation between cells, passing data between the different mesh elements is more complicated and more prone to error. For example, values from one or more bordering inviscid fluid cells may be passed to a neighboring boundary-layer fluid cell. One or more inviscid fluid cells must be selected and the values interpolated depending on the degree of overlap between the cells. These techniques tend to introduce error into the simulation and reduce the robustness of the solution.

Figure 5:
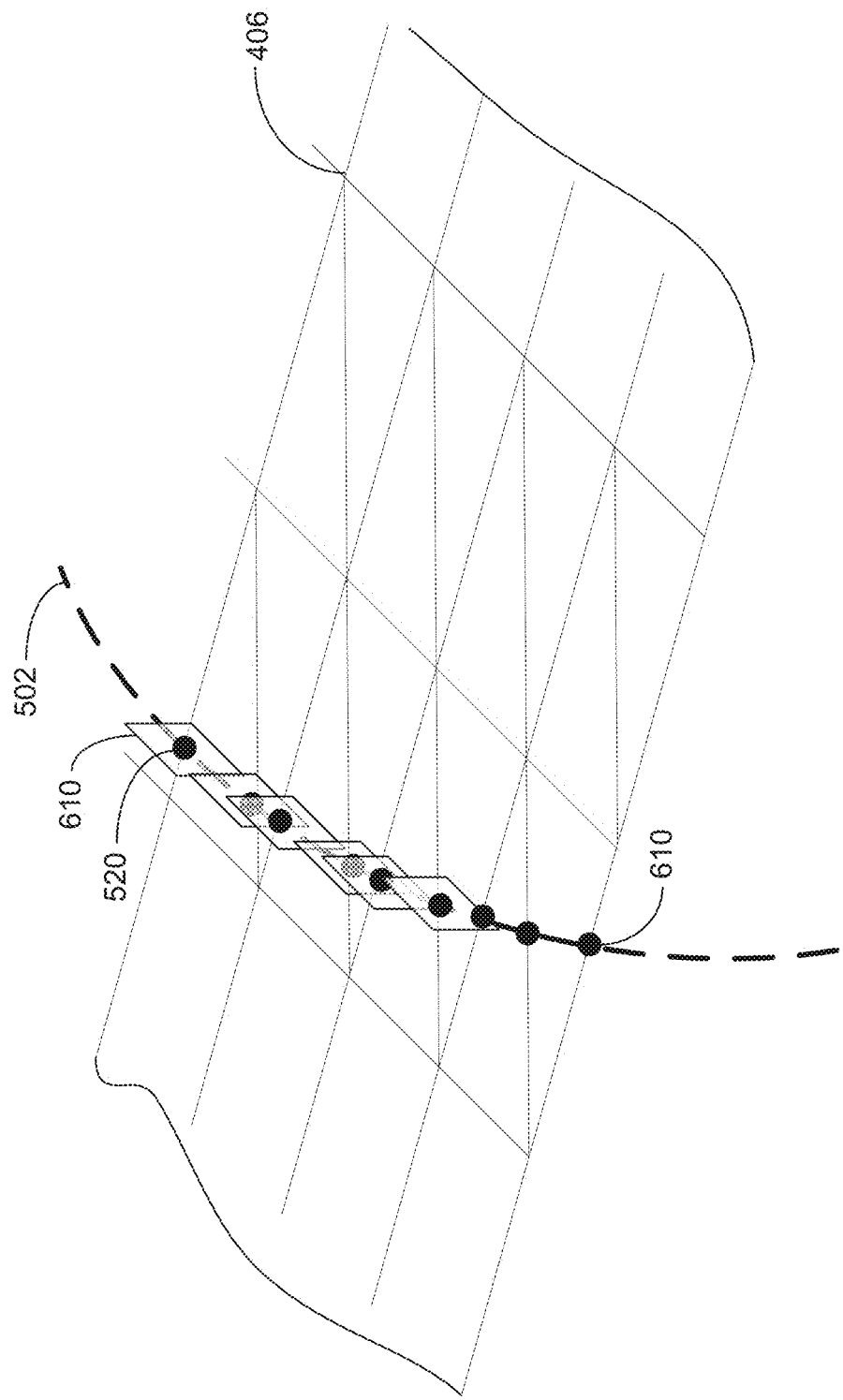
FIG. 5 depicts an exemplary fluid-flow mesh and boundary-layer prediction points.
Figure 6:
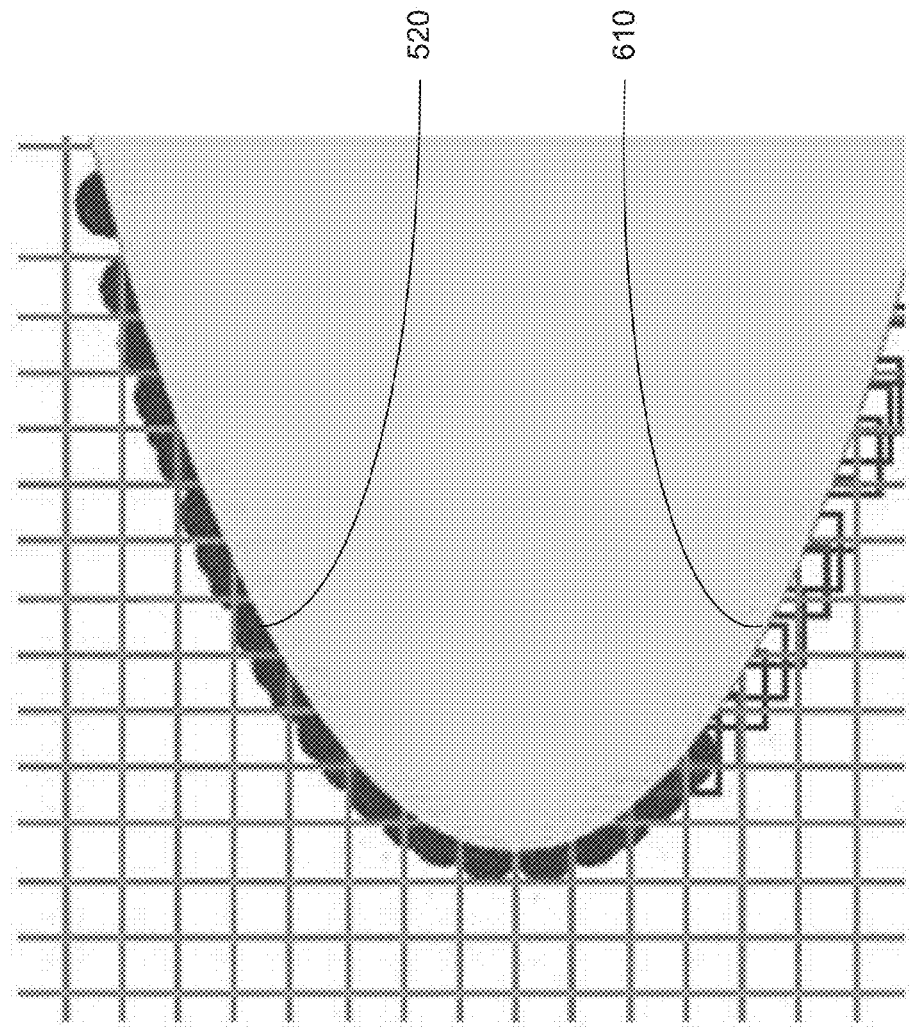
FIG. 6 depicts a cross-sectional view of an exemplary fluid-flow mesh and boundary-layer prediction points.

In some cases, the boundary-layer mesh can be derived from the intersection of the fluid-flow mesh 402 and the surface mesh 406. As shown in FIG. 5, a set of boundary-layer fluid cells may be defined according to the location of surface mesh elements with respect to an intersecting plane of fluid cells of the fluid-flow mesh. FIG. 5 depicts a surface mesh 406 of the wing surface intersected by a two-dimensional strip 502 representing the centerline of a plane of fluid cells of the fluid-flow mesh. A boundary-layer prediction point 520 is created at the intersection of the strip 502 and the border of each intersected surface mesh element. The boundary-layer prediction points 520 can be used to construct a local boundary-layer fluid-flow mesh with a boundary-layer fluid cell 610 centered on each boundary-layer prediction point 520. The resulting boundary-layer fluid cells 610 can be used to simulate the boundary-layer portion of the simulated fluid flow. Note that in this example, the boundary-layer mesh is one cell thick as viewed along the wing cross-section. See, for example, FIG. 6 depicting boundary-layer fluid cells 610 centered on boundary-layer prediction points 520.

Using the boundary-layer fluid cells 610, a boundary-layer CFD simulation module can be coupled with an inviscid CFD simulation module to predict the fluid property values on and around the wing. In one example, an inviscid CFD simulation module determines a local pressure, fluid density, and local velocity values for each fluid cell in the fluid-flow mesh. The boundary-layer CFD simulation module receives fluid property values from neighboring inviscid fluid cells. If there is more than one neighboring inviscid fluid cell present, the boundary-layer CFD module typically interpolates the inviscid fluid property values to combine the results from the multiple neighboring inviscid fluid cells. As discussed above, interpolation techniques may introduce error into the simulation due to errors in the interpolation and approximating the contributions from multiple inviscid fluid cells.

Using, for example, equations 1 and 2 above, the boundary-layer CFD module determines the properties of the simulated fluid flow in the boundary-layer region. The boundary-layer CFD simulation module returns fluid properties and/or a transpiration flux value representing a fictitious fluid flow into or out of the wing. As mentioned above, there may be more than one neighboring inviscid fluid cell that receives these values from a corresponding boundary-layer fluid cell. It is also likely that there is more than one boundary-layer fluid cell neighboring a bordering inviscid fluid cell. This mismatch between flow cells may generate additional error and/or model instability.

Additional problems may arise because the boundary-layer prediction points 520 are not evenly spaced along the two-dimensional strip 502 representing the centerline of a plane of fluid cells of the fluid-flow mesh. As shown in FIGS. 5 and 6, boundary-layer fluid cells 610, which are centered on the boundary-layer prediction points 520, are also unevenly spaced, resulting in gaps or bunching in the boundary-layer fluid-flow mesh. In fact, the spacing of the boundary-layer fluid cells is often much finer than the spacing of the inviscid fluid-flow mesh. In practice, the mismatched spacing requires numerical smoothing or averaging to obtain more consistent boundary-layer CFD simulation module results. However, the smoothing can introduce further error in the simulation and in some cases may produce false or inaccurate predictions of the fluid behavior.

In summary, because the values produced by each CFD simulation module are not passed to a corresponding fluid cell with a one-to-one correlation, error and instability are introduced into the computer model. Error due to interpolation and smoothing also tends to become exacerbated as the inviscid and boundary-layer CFD simulation modules are iterated multiple times.

As suggested above, many of these errors may be overcome or greatly reduced by establishing a one-to-one correlation between an inviscid fluid cell and a boundary-layer fluid cell. The following technique provides one example of how a one-to-one correlation can be maintained for computer models using an inviscid fluid-flow mesh and a surface mesh that do not align.

3. Multiple CFD Simulation Modules with One-to-One Fluid Cell Correlation

Figure 9:
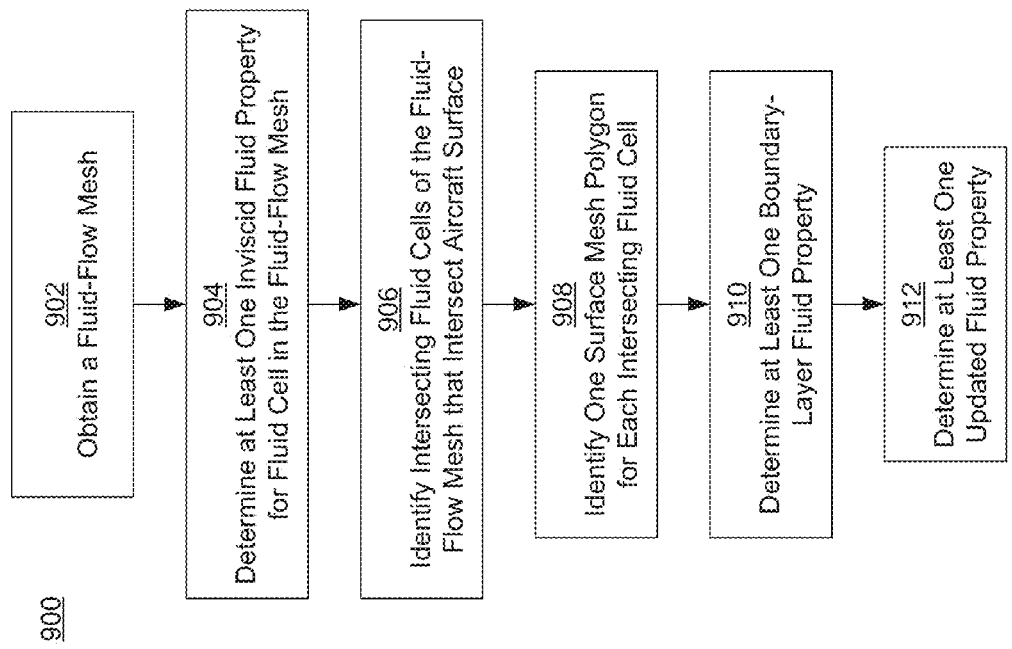
FIG. 9 depicts an exemplary schematic diagram for simulating a fluid flow using inviscid and viscous simulation modules.

FIG. 9 depicts an exemplary process 900 for simulating a fluid flow using both an inviscid CFD simulation module and a viscous CFD simulation module. Using the process 900, explained below, a one-to-one correlation is determined between the fluid cells used by each CFD simulation module.

In step 902, a fluid-flow mesh is obtained for simulating the inviscid portion of the fluid flow. In one exemplary embodiment, as shown in FIG. 4, the fluid-flow mesh is a Cartesian mesh generated around an aircraft surface, such as a wing surface. The Cartesian mesh has cube or cuboid fluid cells. Typically, the Cartesian mesh surrounds the aircraft surface, but it is not necessary to do so.

In step 904, an inviscid CFD simulation module is used to determine inviscid fluid properties for each fluid cell in the fluid-flow mesh. The inviscid CFD simulation module may use the Euler-based method in equation 3 to determine the inviscid fluid properties. The inviscid fluid properties include but are not limited to: local velocity vector, fluid pressure, and fluid density.

Figure 7:
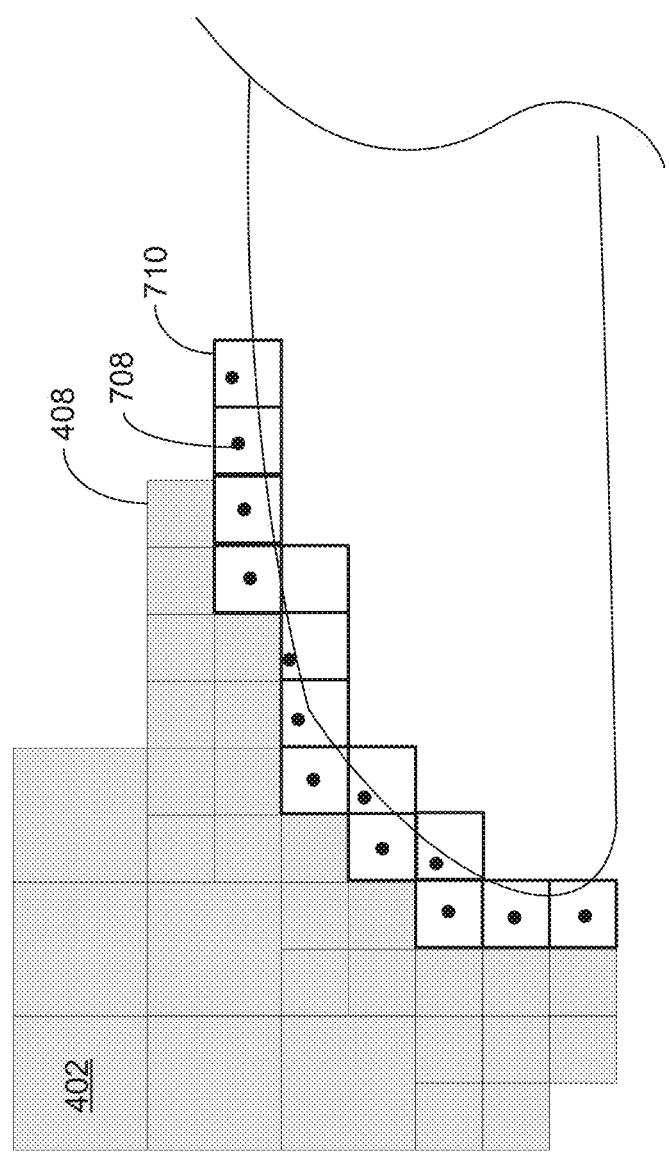
FIG. 7 depicts a cross-sectional view of an exemplary fluid-flow mesh with partially intersecting fluid cells.

In step 906, fluid cells of the fluid-flow mesh that intersect the surface of the aircraft surface are identified. For example, FIG. 7 depicts a cross section of a wing surface (an exemplary aircraft surface). The cross section depicted in FIG. 7 is taken along the center of a plane of fluid cells 408 of fluid-flow mesh 402, which is depicted as being a Cartesian mesh. As shown in FIG. 7, some of the fluid cells 408 of the fluid-flow mesh 402 intersect the surface of the wing. Fluid cells that at least partially intersect the wing surface are designated as intersecting fluid cells 710.

While FIG. 7 depicts a cross section of a cut created by the intersection of the plane of fluid cells 408 and the wing surface, a similar cut can be created using nearly any arbitrary plane that intersects the wing surface. In some cases, the cut may be defined as the intersection between a spherical or cylindrical surface and the wing surface.

Figure 8:
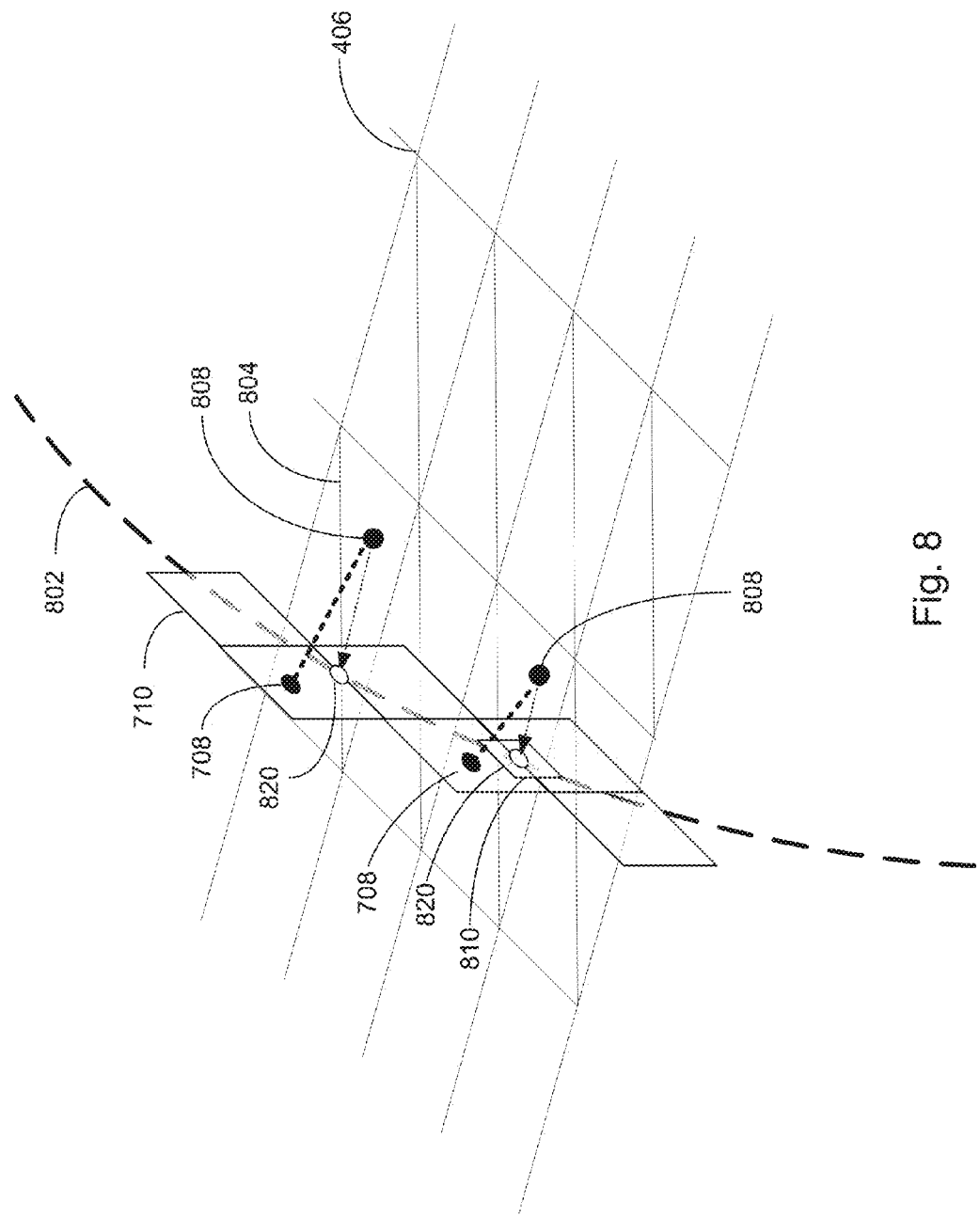
FIG. 8 depicts an exemplary mapping of cells in an exemplary fluid-flow mesh to polygons in an exemplary surface mesh.

In step 908, one representative surface mesh polygon is identified for each intersecting fluid cell. The representative surface mesh polygon should be selected based on its proximity to the intersecting fluid cell. FIG. 8 depicts the same set of intersecting fluid cells 710 intersecting a surface mesh 406 representing the wing surface shown in FIG. 7. A two-dimensional strip 802 represents the intersection of the center of a plane of fluid cells of the fluid-flow mesh and the surface mesh 406.

In some cases, a centroid 708 of each partially intersecting fluid cell 710 is defined. The centroid 708 is the geometric centroid of the portion of the intersecting fluid cell 710 that is outside the wing surface. A centroid 808 is also defined for nearby surface mesh polygons. A surface mesh polygon having a centroid 808 that is closest to the intersecting fluid cell centroid 708 is selected as the representative surface mesh polygon 804. In this example, the centroid 808 of the representative surface mesh polygon 804 is associated with a point on the plane of fluid cells of the fluid-flow mesh intersecting the surface mesh 406. The associated point for each respective selected surface mesh polygon is used as the boundary-layer prediction point 820.

To determine the associated point to be used as the boundary-layer prediction point 820, the intersection of the plane of fluid cells of the fluid-flow mesh and the surface mesh may be represented by an intersection line composed of a series of short line segments. Each line segment represents the intersection between the plane of fluid cells and an intersected surface mesh polygon. The end of each segment falls either on the edge of an intersecting fluid cell or an intersected surface mesh polygon. For a given centroid 808 of a representative surface mesh polygon 804, a line segment is identified that has a midpoint that is closest to the given centroid 808. This midpoint is then used as the associated boundary-layer prediction point 820.

A boundary-layer fluid cell 810 may be centered on each boundary-layer prediction point 820. Using this technique, a single boundary-layer fluid cell 810 is selected for each intersecting fluid cell 710. Thus, there is a one-to-one correlation between intersecting inviscid fluid cells and boundary-layer fluid cells, simplifying the data transfer between the two simulations.

In step 910, at least one boundary-layer fluid property is determined for each boundary-layer prediction point 820 or boundary-layer fluid cell 810. The at least one boundary-layer fluid property for a boundary-layer prediction point 820 or boundary-layer fluid cell 810 is determined using a viscous or boundary-layer CFD simulation module and the inviscid fluid properties of the corresponding intersecting fluid cell 710. For example, field equations 1 and 2 described above can be used to determine a momentum thickness using inviscid fluid properties of the corresponding intersecting fluid cell 710.

In some cases, the at least one boundary-layer fluid property includes a boundary-layer thickness value and corresponding transpiration flux value. The boundary-layer thickness value represents the distance from the surface of the aircraft where the fluid flow can be treated as inviscid. For example, as discussed above, the fluid flow may be treated as inviscid if the velocity profile of the fluid flow is uniform enough to ignore the viscosity of the fluid.

A transpiration flux value can also be used to approximate the thickness of the boundary layer by introducing a fictitious flow of air out of the aircraft surface over an arc length along the boundary-layer strip solution. The introduction of the fictitious flow modifies the inviscid simulated flow near the aircraft surface so as to approximate the presence of a boundary-layer flow having an appropriate thickness. As the magnitude of the transpiration flux increases, the fictitious flow increases, simulating a thicker boundary layer. In some cases, the transpiration flux can be used to create a fictitious flow of air into the aircraft surface (negative flux), thereby reducing the thickness of the boundary layer.

The transpiration flux can be determined using the output of the Drela boundary-layer technique described in equations 1 and 2, above. For example, the transpiration flow velocity $W_{iw}$ of the transpiration flux can be determined using:

$$W_{iw} = \frac{1}{\rho_{iw}} \frac{d}{ds}(\rho_{iw} U_{iw} \delta^*),$$ Equation 4 where $\rho_{iw}$ is the density of the fluid flow at the aircraft surface, $U_{iw}$ is the velocity of the fluid flow at the aircraft surface, $\delta^*$ is the computed boundary layer displacement thickness, and s is the arc length along the boundary-layer strip solution.

Equation 4 is taken from Lock, R. C., and Williams, B. R., "Viscous-Inviscid Interactions in External Aerodynamics," Prog. Aerospace Sci., Vol. 24, 1987, pp. 51-171. Thus, the transpiration mass flux (density $\rho_{iw}$ times the transpiration flow velocity $W_{iw}$) is equal to the rate of change of the product of the local density $\rho_{iw}$, local velocity $U_{iw}$, and boundary layer displacement thickness $\delta^*$ along the solution strip. A finite difference method can be used to compute the derivative in equation 4. For example, the neighboring solution points along the boundary-layer strip can be used with a second order, backward Lagrange polynomial formulation to compute the derivatives.

In step 912, at least one fluid property of at least one fluid cell of the fluid-flow mesh is updated to account for the changes in the boundary-layer fluid flow. For example, as described above, the transpiration flux introduces a fictitious fluid flow out of the aircraft surface. An inviscid CFD simulation module can then be used to update the fluid properties of the fluid cells of the fluid-flow mesh based on the fictitious fluid flow introduced by the transpiration flux.

Figure 10:
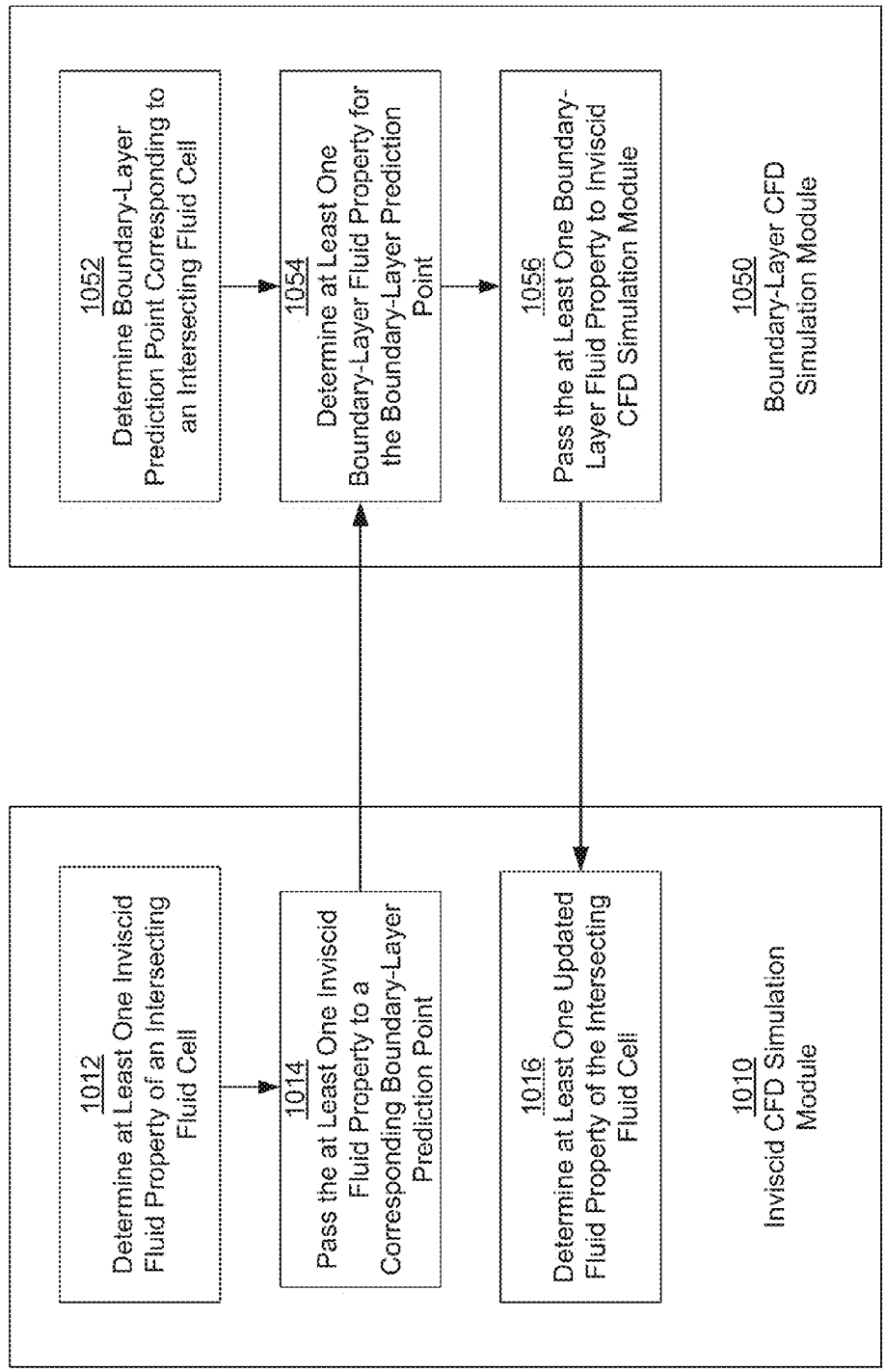
FIG. 10 depicts an exemplary exchange between the inviscid CFD simulation module and the boundary-layer CFD module.

FIG. 10 depicts an exemplary exchange between the inviscid CFD simulation module 1010 and the boundary-layer CFD module 1050. FIG. 10 also depicts the operations performed by the CFD module 1010 (i.e., operations 1012, 1014, 1016) and the boundary-layer CFD module 1050 (i.e., operations 1052, 1054, 1056).

As mentioned above, the inviscid CFD simulation module 1010 uses a fluid-flow mesh, such as a Cartesian mesh, of fluid cells to represent the volume of fluid around a aircraft surface, such as a wing surface, using a suitable field equation, such as equation 3 above, to predict the fluid properties for each fluid cell in the fluid-flow mesh. In this example, the inviscid CFD simulation module 1010 can be nearly any existing Cartesian inviscid flow simulation module.

As described above in reference to FIGS. 7 and 8, a set of intersecting fluid cells are identified that intersect a surface mesh 406 representing the aircraft surface. In operation 1012, the inviscid CFD simulation module 1010 determines at least one inviscid fluid property of at least one intersecting fluid cell 710 (FIGS. 7 and 8) of the set of intersecting fluid cells.

In operation 1052, one boundary-layer prediction point 820 (FIG. 8) is determined based on the location of the intersecting fluid cell 710 (FIG. 8). As described above, for each selected intersecting fluid cell 710 (FIG. 8), one representative triangulated surface mesh polygon 804 (FIG. 8) is selected based on the proximity of the surface mesh polygon 804 (FIG. 8). A point in the representative triangulated surface mesh polygon, such as the centroid 808 (FIG. 8), is then associated with a point on the plane created by the intersecting fluid cells. The associated point can be designated as a boundary-layer prediction point 820 (FIG. 8), and can be used to define a boundary-layer fluid cell 810 (FIG. 8). Thus, for each intersecting fluid cell, there is one corresponding boundary-layer fluid cell.

In operation 1014, at least one inviscid fluid property of the intersecting fluid cell 710 (FIG. 8) is passed to the corresponding boundary-layer prediction point 820 (FIG. 8) or boundary-layer fluid cell 810 (FIG. 8). The at least one inviscid fluid property includes, for example, local pressure, fluid density, and local velocity values.

In operation 1054, the boundary-layer CFD simulation module 1050 uses the at least one inviscid fluid property to predict the at least one boundary-layer fluid property for the boundary-layer prediction point 820 (FIG. 8) or boundary-layer fluid cell 810 (FIG. 8). As described above, the boundary-layer CFD module 1050 may use the field equations 1 and 2 above to predict one or more boundary-layer fluid properties. In some cases, the results of the boundary-layer CFD simulation module 1050 can then be used to determine a boundary-layer thickness or transpiration flux value for the boundary-layer prediction point 820 (FIG. 8) or boundary-layer fluid cell 810 (FIG. 8).

In operation 1056, one or more boundary-layer fluid properties are passed to the inviscid simulation module 1010. As described above, in some cases a transpiration flux value is used to introduce a fictitious flow back into the inviscid fluid-flow cell.

In operation 1016, the inviscid CFD simulation module 1010 uses the one or more boundary-layer fluid properties to determine at least one updated fluid property of at least one fluid cell of the fluid-flow mesh. By updating at least one fluid property of the fluid cell, the fluid-flow simulation accounts for influences due to the boundary-layer flow conditions. In this way, fluid properties (e.g., inviscid fluid property and boundary-layer fluid property) can be passed between inviscid and boundary-layer CFD simulation modules without requiring interpolation or smoothing.

Depending on the size of the fluid cells (coarseness of the fluid-flow mesh) and the curvature of the wing surface, the simulation may become choppy or stepped and, thus, in some cases, smoothing may be used to refine the results. However, the smoothing is less error inducing than as described for the techniques above without a one-to-one correlation between inviscid fluid cells and boundary-layer fluid cells.

The exemplary exchange between the inviscid CFD simulation module 1010 and the boundary-layer CFD module 1050 shown in FIG. 10 is merely an illustrative example. In some cases, modules other than the inviscid CFD simulation module 1010 and the boundary-layer CFD module 1050 perform one or more of the operations described above. In particular, determining the intersecting fluid cell and operation 1052 for determining the boundary-layer prediction point may be performed by modules other than the CFD simulation module 1010 and the boundary-layer CFD module 1050.

Depending on the particular simulation, the process described above may be iterated several times until a steady-state solution is reached. Thus, the data exchange between the CFD simulation module 1010 and the boundary-layer CFD module 1050 may occur multiple times as the simulation is iterated.

4. Computer and Computer Network System

Figure 11:
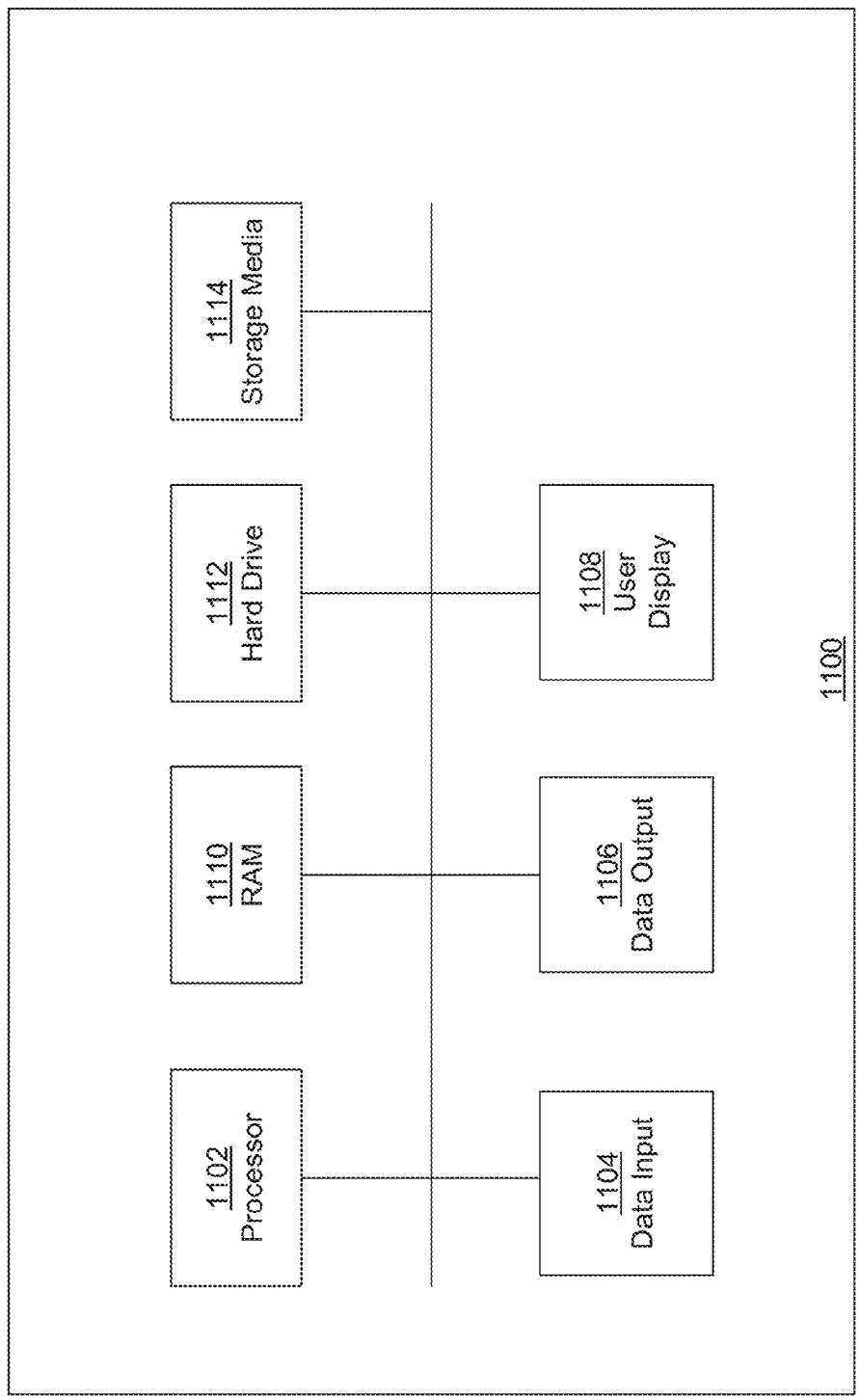
FIG. 11 depicts an exemplary computer system for simulating a fluid flow over an aircraft surface.

The embodiments described herein are typically implemented as computer software (computer-executable instructions) executed on a processor of a computer system. FIG. 11 depicts an exemplary computer system 1100 configured to perform any one of the above-described processes. Computer system 1100 may include the following hardware components: processor 1102, data input devices (e.g., keyboard, mouse, keypad) 1104, data output devices (e.g., network connection, data cable) 1106, and user display (e.g., display monitor) 1108. The computer system also includes non-transitory memory components including random access memory (RAM) 1110, hard drive storage 1112, and other computer-readable storage media 1114.

Processor 1102 is a computer processor capable of receiving and executing computer-executable instructions for performing any of the processes described above. Computer system 1100 may include more than one processor for performing the processes. The computer-executable instructions may be stored on one or more types of non-transitory storage media including RAM 1110, hard drive storage 1112, or other computer-readable storage media 1114. Other computer-readable storage media 1114 include, for example, CD-ROM, DVD, magnetic tape storage, magnetic disk storage, solid-state storage, and the like.

Figure 12:
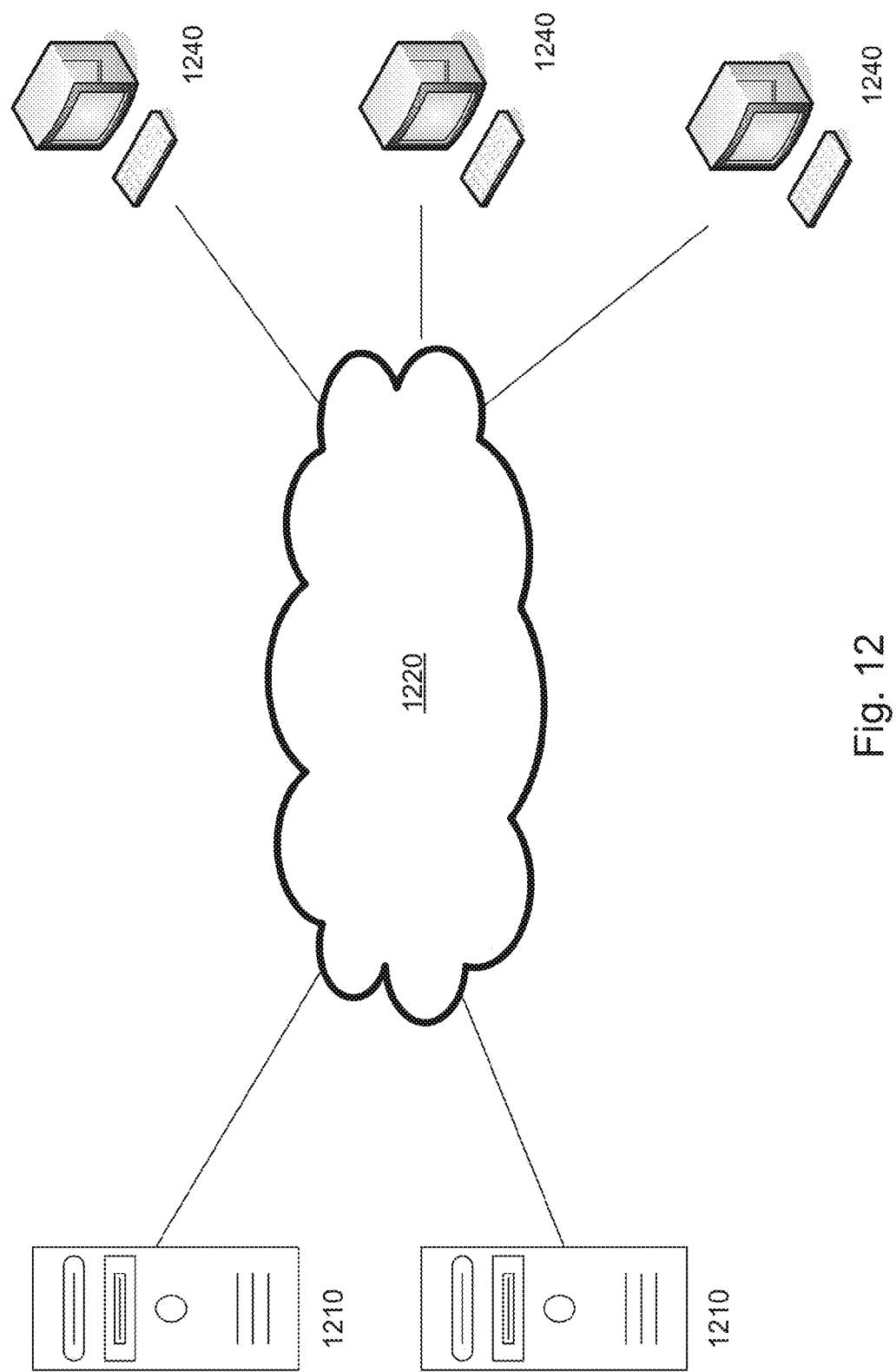
FIG. 12 depicts an exemplary computer network.

FIG. 12 depicts an exemplary computer network for distributing the processes described above to multiple computers at remote locations. One or more servers 1210 may be used to perform portions of the process described above. For example, one or more servers 1210 may store and execute computer-executable instructions for receiving information for generating a computer-generated simulation. The one or more servers 1210 are specially adapted computer systems that are able receive input from multiple users in accordance with a web-based interface. The one or more servers 1210 are able to communicate directly with one another using a computer network 1220 including a local area network (LAN) or a wide area network (WAN), such as the Internet.

One or more client computer systems 1240 provide an interface to one or more system users. The client computer systems 1240 are capable of communicating with the one or more servers 1210 over the computer network 1220. In some embodiments, the client computer systems 1240 are capable of running a web browser that interfaces with a web-enabled system running on one or mover server machines 1210. The web browser is used for accepting input data from the user and presenting a display to the user in accordance with the exemplary user interface described above. The client computer 1240 includes a computer monitor or other display device for presenting information to the user. Typically, the client computer 1240 is a computer system in accordance with the computer system 1100 depicted in FIG. 11.

Although the invention has been described in considerable detail with reference to certain embodiments thereof, other embodiments are possible, as will be understood by those skilled in the art.

We claim:

1. A computer-implemented method of generating a fluid-flow simulation over a computer-generated surface, the computer-generated surface comprised of a surface mesh of surface mesh polygons, the method comprising:
    obtaining a fluid-flow mesh for simulating a fluid flow over the surface, the fluid-flow mesh comprising a plurality of fluid cells;
    determining at least one inviscid fluid property for each of the fluid cells using an inviscid fluid simulation that does not simulate fluid viscous effects;
    identifying a set of intersecting fluid cells of the plurality of fluid cells, wherein the set of intersecting fluid cells intersects the surface;
    identifying a set of surface mesh polygons of the surface mesh, wherein each surface mesh polygon of the set of surface mesh polygons corresponds to an intersecting fluid cell of the set of intersecting fluid cells, and wherein a number of surface mesh polygons of set of surface mesh polygons is fewer than a total number of surface mesh polygons that are intersected by the set of intersecting fluid cells;
    determining at least one boundary-layer fluid property for at least one identified surface mesh polygon using the at least one inviscid fluid property of the corresponding intersecting fluid cell and a boundary-layer simulation that simulates fluid viscous effects.

2. The computer-implemented method of claim 1, further comprising:
    determining at least one updated fluid property for the intersecting fluid cell of the set of intersecting fluid cells using the at least one boundary-layer fluid property and the inviscid fluid simulation.

3. The computer-implemented method of claim 1, wherein identifying the set of surface mesh polygons comprises:
obtaining a centroid of the intersecting fluid cell of the set of intersecting fluid cells;
identifying a surface mesh polygon having a centroid that is closest to the centroid of the intersecting fluid cell.

4. The computer-implemented method of claim 3, wherein the centroid of the intersecting fluid cell is the centroid of a region of the intersecting fluid cell that is outside of the surface.

5. The computer-implemented method of claim 1, wherein the at least one boundary-layer fluid property includes a boundary-layer thickness value, the boundary-layer thickness value representing a distance from the surface where fluid viscous effects can be ignored.

6. The computer-implemented method of claim 1, wherein the at least one boundary-layer fluid property includes a transpiration flux value, the transpiration flux value representing a direction and an amount of fluid flow originating from the surface.

7. The computer-implemented method of claim 1, wherein the inviscid fluid simulation is an Euler-based flow simulation.

8. The computer-implemented method of claim 1, wherein the at least one inviscid fluid property includes a fluid velocity vector, a fluid density value, and a fluid pressure value.

9. The computer-implemented method of claim 1, wherein the computer-generated surface is an aircraft surface.

10. A computer-implemented method of generating a fluid-flow simulation over a computer-generated surface, the computer-generated surface comprised of a surface mesh of surface mesh polygons, the method comprising:
obtaining a fluid-flow mesh for simulating a fluid flow over the surface, the fluid-flow mesh comprising a plurality of fluid cells;
determining at least one inviscid fluid property for each of the fluid cells using an inviscid fluid simulation that does not simulate fluid viscous effects;
identifying an intersecting fluid cell of the plurality of fluid cells that intersects the surface;
determining a single boundary-layer prediction point for the intersecting fluid cell resulting in a one-to-one correlation between the intersecting fluid cell and the boundary-layer prediction point; and
determining at least one boundary-layer fluid property for the boundary-layer prediction point using the at least one inviscid fluid property of the intersecting fluid cell.

11. A non-transitory computer-readable storage medium comprising computer-executable instructions for generating a fluid-flow simulation over a computer-generated surface, the computer-generated surface comprised of a surface mesh of surface mesh polygons, the instructions for:
obtaining a fluid-flow mesh for simulating a fluid flow over the surface, the fluid-flow mesh comprising a plurality of fluid cells;
determining at least one inviscid fluid property for each of the fluid cells using an inviscid fluid simulation that does not simulate fluid viscous effects;
identifying a set of intersecting fluid cells of the plurality of fluid cells, wherein the set of intersecting fluid cells intersects the surface;
identifying a set of surface mesh polygons of the surface mesh, wherein each surface mesh polygon of the set of surface mesh polygons corresponds to an intersecting fluid cell of the set of intersecting fluid cells, and wherein a number of surface mesh polygons of set of surface mesh polygons is fewer than a total number of surface mesh polygons that are intersected by the set of intersecting fluid cells; and
determining at least one boundary-layer fluid property for at least one identified surface mesh polygon using the at least one inviscid fluid property of the corresponding intersecting fluid cell and a boundary-layer simulation that simulates fluid viscous effects.

12. The computer-readable storage medium of claim 11, the instructions further comprising:
determining at least one updated fluid property for the intersecting fluid cell of the set of intersecting fluid cells using the at least one boundary-layer fluid property and the inviscid fluid simulation.

13. The computer-readable storage medium of claim 11, wherein identifying the set of surface mesh polygons comprises instructions for:
obtaining a centroid of the intersecting fluid cell of the set of intersecting fluid cells;
identifying a surface mesh polygon having a centroid that is closest to the centroid of the intersecting fluid cell.

14. The computer-readable storage medium of claim 13, wherein the centroid of the intersecting fluid cell is the centroid of a region of the intersecting fluid cell that is outside of the surface.

15. The computer-readable storage medium of claim 11, wherein the at least one boundary-layer fluid property includes a boundary-layer thickness value, the boundary-layer thickness value representing a distance from the surface where fluid viscous effects can be ignored.

16. The computer-readable storage medium of claim 11, wherein the at least one boundary-layer fluid property includes a transpiration flux value, the transpiration flux value representing a direction and an amount of fluid flow originating from the surface.

17. The computer-readable storage medium of claim 11, wherein the inviscid fluid simulation is an Euler-based flow simulation.

18. The computer-readable storage medium of claim 11, wherein the at least one inviscid fluid property includes a fluid velocity vector, a fluid density value, and a fluid pressure value.

19. The computer-readable storage medium of claim 11, wherein the computer-generated surface is an aircraft surface.

20. A non-transitory computer-readable storage medium comprising computer-executable instructions for generating a fluid-flow simulation over a computer-generated surface, the computer-generated surface comprised of a surface mesh of surface mesh polygons, the instructions comprising instructions for:
obtaining a fluid-flow mesh for simulating a fluid flow over the surface, the fluid-flow mesh comprising a plurality of fluid cells;
determining at least one inviscid fluid property for each of the fluid cells using an inviscid fluid simulation that does not simulate fluid viscous effects;
identifying an intersecting fluid cell of the plurality of fluid cells that intersects the surface;
determining a single boundary-layer prediction point for the intersecting fluid cell resulting in a one-to-one correlation between the intersecting fluid cell and the boundary-layer prediction point; and
determining at least one boundary-layer fluid property for the boundary-layer prediction point using the at least one inviscid fluid property of the intersecting fluid cell.

* * * * *

UNITED STATES PATENT AND TRADEMARK OFFICE
CERTIFICATE OF CORRECTION

| | |
|---|---|
| PATENT NO. | : 8,935,140 B2 |
| APPLICATION NO. | : 13/887189 |
| DATED | : January 13, 2015 |
| INVENTOR(S) | : David L. Rodriguez et al. |

It is certified that error appears in the above-identified patent and that said Letters Patent is hereby corrected as shown below:

In the Specification

In column 1, line 11, please insert the following header and paragraph:

--STATEMENT REGARDING FEDERALLY SPONSORED RESEARCH OR DEVELOPMENT

This invention was made with Government support under contract NNL08AA08C awarded by NASA. The Government has certain rights in the invention.--

Signed and Sealed this
Fifth Day of May, 2015

Michelle K. Lee
*Director of the United States Patent and Trademark Office*